(12) United States Patent
Tortorella (10) Patent No.: US 6,544,417 B1
(45) Date of Patent: Apr. 8, 2003

(54) LOW BINDING LIQUID RETAINING AND FILTERING DEVICE

(75) Inventor: Micky Daniel Tortorella, Newark, DE (US)

(73) Assignee: DuPont Pharmaceuticals, Inc., Wilmington, DE (US)

( * ) Notice: Subject to any disclaimer, the term of this patent is extended or adjusted under 35 U.S.C. 154(b) by 0 days.

(21) Appl. No.: 09/616,597

(22) Filed: Jul. 14, 2000

Related U.S. Application Data (60) Provisional application No. 60/145,527, filed on Jul. 16, 1999.

(51) Int. Cl.[7] ............................................. B01D 63/00
(52) U.S. Cl. ................. 210/321.75; 210/477; 422/101; 422/102; 422/104
(58) Field of Search ............................... 422/101, 104, 422/102, 68.1, 799; 210/321.75, 477, 500.36

(56) References Cited

U.S. PATENT DOCUMENTS

| | | | |
|---|---|---|---|
| 3,661,265 A | 5/1972 | Greenspan | 210/359 |
| 3,870,639 A | 3/1975 | Moore et al. | 210/359 |
| 4,136,036 A | 1/1979 | Columbus | 210/516 |
| 4,214,993 A | 7/1980 | Forsythe, Jr. et al. | 210/282 |
| 4,427,415 A | 1/1984 | Cleveland | 436/57 |
| 4,436,631 A | 3/1984 | Graham, Jr. et al. | 210/772 |
| 4,623,461 A | 11/1986 | Hossom et al. | 210/445 |
| 4,683,058 A | 7/1987 | Lyman et al. | 210/359 |
| 4,777,021 A | 10/1988 | Wertz et al. | 422/101 |
| 4,891,134 A | 1/1990 | Vcelka | 210/359 |
| 4,902,481 A | 2/1990 | Clark et al. | 422/101 |
| 4,990,253 A | 2/1991 | Vcelka | 210/359 |
| 5,104,533 A | 4/1992 | Szabados | |
| 5,516,564 A | 5/1996 | Root et al. | 428/35.7 |
| 5,733,449 A * | 3/1998 | Bowers et al. | |
| 5,853,894 A * | 12/1998 | Brown | |
| 5,863,791 A | 1/1999 | Baldszun | 435/288.1 |
| 5,882,943 A | 3/1999 | Aldeen | 436/178 |
| 5,888,831 A | 3/1999 | Gautsch | 436/177 |
| 5,935,858 A * | 8/1999 | Herst | |
| 6,017,496 A * | 1/2000 | Nova et al. | |
| 6,103,195 A | 8/2000 | Shukla et al. | 422/70 |
| 6,159,368 A * | 12/2000 | Moring et al. | |
| 6,200,474 B1 * | 3/2001 | Kopacikewicz et al. | |
| 6,269,957 B1 * | 8/2001 | Bowers et al. | |
| 6,287,872 B1 | 9/2001 | Schurenberg et al. | 436/181 |
| 6,309,605 B1 * | 10/2001 | Zermani | |

FOREIGN PATENT DOCUMENTS

| | | |
|---|---|---|
| EP | 1 053 784 | 11/2000 |
| EP | 1 151 793 | 11/2001 |
| WO | 94/25161 | 11/1994 |

OTHER PUBLICATIONS

J. Adhesion, 1998 vol. 66, pp. 229–249; "Creating Smart Polymer Surfaces with Selective Adhesion Properties"; J.T. Koberstein, et al.

* cited by examiner

Primary Examiner—Ana Fortuna
(74) Attorney, Agent, or Firm—Nields & Lemack (57) ABSTRACT

This invention is directed to filtrate-holder and reversible-well collection plates composed of polypropylene and Teflon® resin, and to their use, in connection with compatible filter units, in high-throughput screening assays for assessing the binding of small molecules to proteins.

5 Claims, 14 Drawing Sheets

LOW BINDING LIQUID RETAINING AND FILTERING DEVICE

This application claims the benefit of the filing dates of U.S. Provisional Application Ser. No. 60/145,527 filed Jul. 16, 1999.

FIELD OF THE INVENTION

This invention relates to novel plate devices for use in high-throughput screening assays.

BACKGROUND OF THE INVENTION

The binding of small molecules and peptides to protein is a very important parameter to measure in the pharmaceutical industry. As pharmaceutical companies strive to design novel small molecules and peptides to treat various ailments ranging from life threatening diseases including cancer, AIDS, and heart disease to cosmetic complaints such as ACNE, age spots and wrinkles, successful administration of these drugs through the circulatory system is critical. Many drugs that have been shown to be very active in vitro assays have failed to show efficacy in animal models and in people because of the high plasma protein binding exhibited by these compounds. When a molecule is highly bound to proteins in the blood the amount of drug available to diffuse into the target tissue is significantly reduced and the efficacy of the drug will inevitably be poor.

Whether a small molecule binds to plasma proteins or not usually depends on the size of the molecule, the amino acid composition and the tertiary structure of the molecule. When a small molecule binds to plasma proteins the interaction usually is a result of strong ionic and hydrophobic interactions. Because blood contains several hundred proteins there is a high probability that any small molecule will exhibit some level of binding. Determining the level of binding therefore is critical and will directly correlate with efficacy of the molecule. Predicting whether a molecule is going to show high or low protein binding based on molecular structure has proven to be very difficult. The only sure way to determine whether or not a molecule will exhibit high or low protein binding is to test the molecule directly in a protein-binding assay.

The most common method used to measure the level of protein binding exhibited by compounds is equilibrium dialysis assays. In such assays, a set concentration of drug (usually 1 μM) is added to a set volume of human plasma (usually 3 ml). The mixture is added to dialysis tubing with a molecular weight cut-off of 30 kDa. The mixture is allowed to incubate in a large volume of water (usually 4 litre) for 24 hours at 37° C. Following the incubation the sample is collected and the concentration of drug is calculated. If the compound is completely unbound to protein, the concentration following dialysis would be 0, if 50% bound the concentration would be 0.5 uM, etc. Although equilibrium dialysis has been shown to be accurate and consistent, it is very time consuming and the number of drugs a researcher can test in one assay is dependent on how many 4-litre beakers he/she can set up. Thus, there is a need for a fast, high-throughput assay in the pharmaceutical industry.

The binding of small molecules even to the plastics such as the polypropylene tubes and plates can be a problem. Polypropylene (PP) is currently considered the best type of commercially available plastic plate based on its low non-specific binding properties and solvent resistance. Even the non-specific binding (NSB) to polypropylene can interfere with the calculation of accurate plasma protein binding values.

SUMMARY OF THE INVENTION

This invention is directed to a substrate having at least one substrate well, such as, a filtration device comprising a polymeric material and an additive to which biomolecules exhibit minimal or no binding. In a preferred embodiment, the filtration device includes a filtrate unit-holder plate and comprises a polyolefin, most preferably polypropylene, and Teflon® resin, most preferably about 2.5% Teflon® resin and about 97.5% polypropylene. Said plate contains a plurality of through-holes, each of which is capable of securely holding a filter unit, such as a Microcon-3, 10, 30 or 100® filter unit (see FIGS. 4, 5, 7 and 8) Said filter unit (see FIG. 1) contains a reservoir and a filter membrane, contained within the filter unit-holder plate. The filter unit also contains a base, which is positioned in an opening in each of the filter unit-holder plate through-holes and into a preferably reversible-well collection plate (see FIGS. 9, 10, 11 and 12). Said "reversible-well collection plate", also comprises a polymeric material and an additive to which biomolecules exhibit minimal or no binding, preferably polypropylene and Teflon® resin (most preferably, again, at about 2.5% Teflon® resin and about 97.5% polypropylene) and also contains a plurality of wells. The collection plate is designed such that its wells can accommodate either end of the filter unit.

The filter unit-holder plate and collection plates, along with the filter units contained therein, are securely fastened together and used in high-throughput screening assays for the binding of small molecules and peptides to proteins. The design of the plates, and their composition, allows for several advantages in the conducting of such screens, as is described herein.

Figure 14:
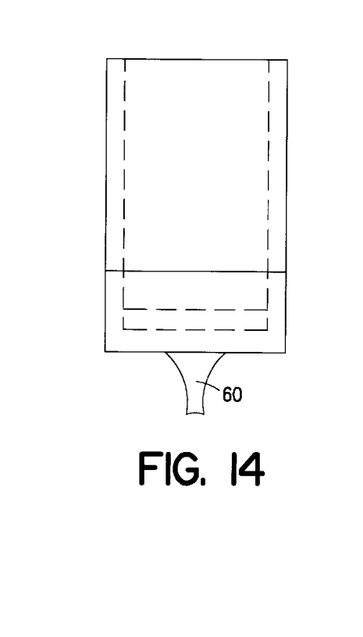
FIGS. 14, 14A—Alternative embodiment using spout to direct flow into the wells of the collection plate.

The filtrate plate device of the present invention consists of a multi-well plate and holder with a unique micro-array format designed to fit 96 Microcon filter units, for example. The holder contains a plurality of through-holes where the filter units are inserted. The ridge of the filter unit lies on top of the through-hole and the bottom (base) of the filter unit passes through. Once the filter units are inserted into the holder, it is placed on top of a multi-well collection plate with the same micro-array format as the holder. The set-up was designed so that several mm of the base of the filter unit protrudes into the wells of the collection plate. This is one way to prevent well to well spill-over during the centrifugation. Alternatively, a spout 60 (FIG. 14) could be used to avoid cross-contamination. The holder/plate sandwich can be spun in a tabletop centrifuge with a swinging bucket to collect the filtrate. The plates were designed to allow stacking of the sandwiches on top of one another to allow more plates to be spun at one time.

In terms of method, sample preparation units are inserted into the custom-designed holder which is then placed on top of the collection plate. 200 ul of sample, for example, is added to the filter units in the presence or absence of the small molecule at a concentration of 1 uM. The plates are placed in a swinging bucket rotor, containing microtiter plate holders. The plates are spun at suitable speeds, such as 3000 g for 30 minutes. The free small molecules (typical molecular weight 300–600 Daltons) readily pass through the filter membrane and pass into the collection well. The bound molecules are retained with the plasma proteins, which range in molecular weight from 20,000 to 500,000 Daltons. The collection plate contains the free compound (filtrate) and the filter reservoir contains the bound compound (retentate). The free compound contained in the filtrate can be determined by mass spectrometry, electrospray or a bioassay.

In order to collect the retentate, another collection plate is placed with the wells facing down on top of filter units. The plate is designed to fit tightly around the open end of the filter units. Next, the holder is inverted and spun an additional five minutes to collect the retentate into the second collection plate. The filtrate is then ready to be analyzed for bound compound. Finally, the filter unit-holder and collection plates are designed with V-grooves on the outer exterior of the plates that make them amenable to automation using robotics.

DETAILED DESCRIPTION OF THE INVENTION

The present invention is directed to a polymeric blend for use in sample preparation, measurement (such as pipettes) or storage (such as tubes) devices which exhibits minimal or no binding to biomolecules (i.e., molecules that affect or are involved in life processes, including synthetic small molecules, peptides, proteins, nucleic acids such as DNA and RNA, oligonucleotides, polysaccharides, lipids, etc.).

The polymeric blend is preferably used in parts of the devices where contact with the liquid sample occurs or is likely to occur. In the preferred embodiment, the device comprises a filter unit holder plate, a filtration device such as the MICROCON filter unit commercially available from Millipore Corporation, and one or more optional collection units. For purposes of illustration, the following discussion will focus on this preferred embodiment, although those skilled in the art will appreciate that the present invention encompasses other sample preparation devices having different configurations.

Figure 1:
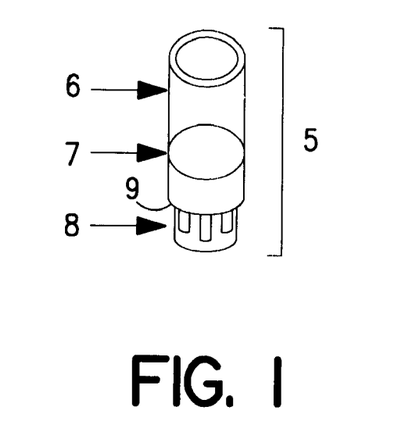
FIGS. 1, 1A—Microcon-10 filter unit (FIG. 1) and collection tube (FIG. 1A). The Microcon-10 filter unit consists of a reservoir which holds up to 500 μl of liquid, the YM membrane and a base which directs the filtrate into the microfuge-collection tube during centrifugation.
Figure 1A:
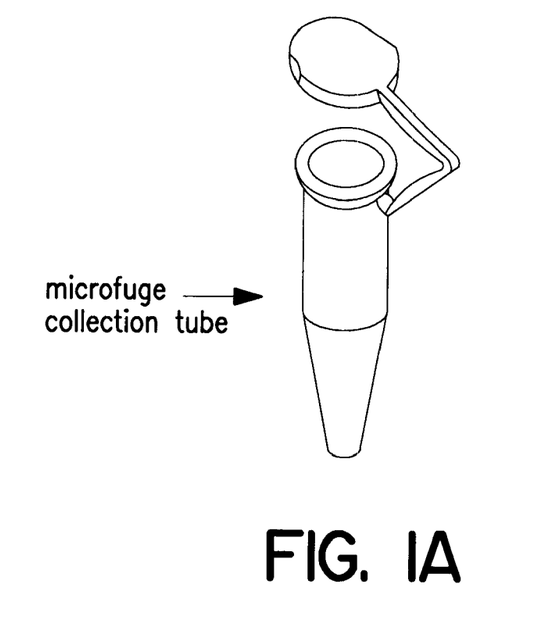
Figure 2:
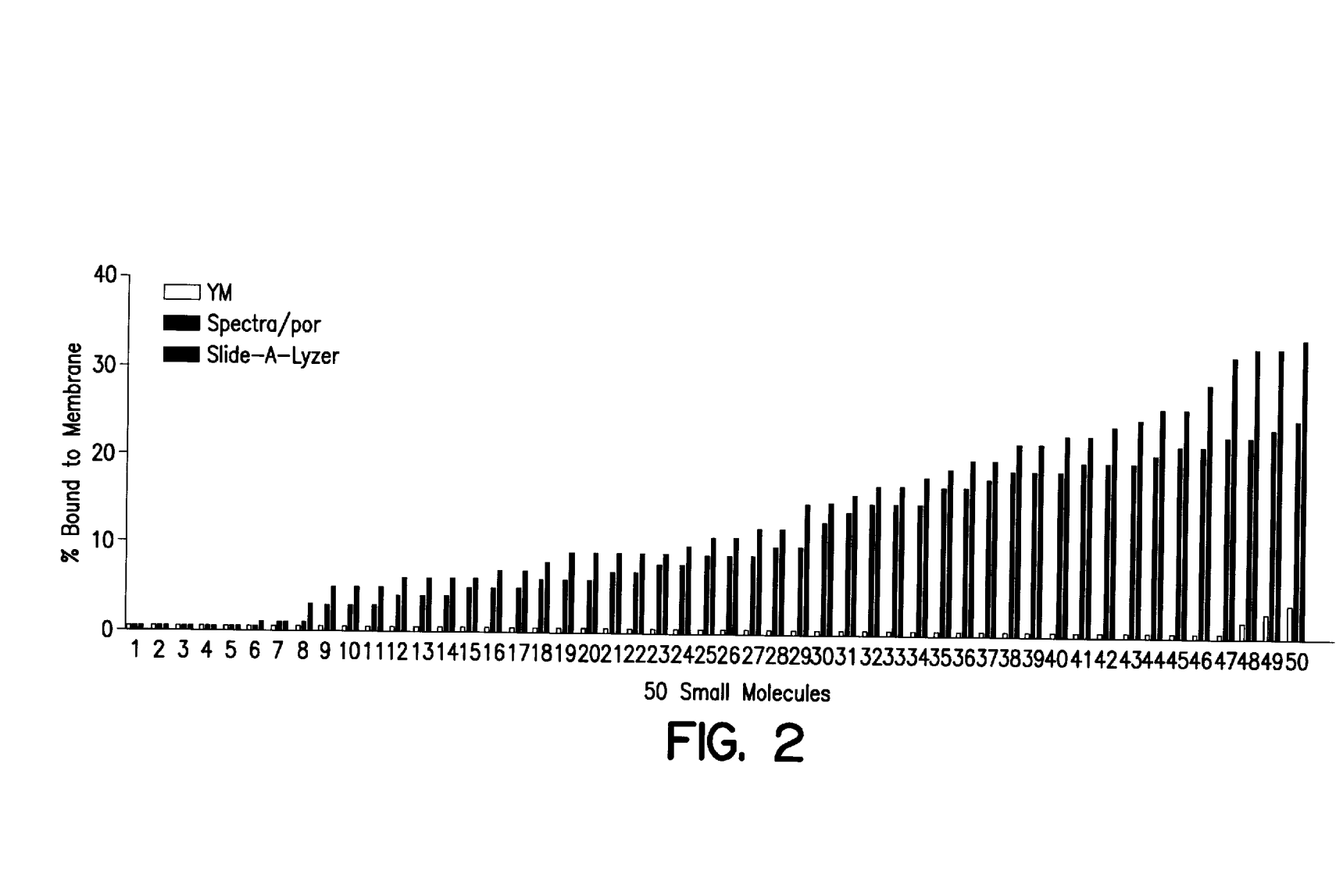
FIG. 2—Binding of Small Molecules to Membranes. The binding of 50 small molecules to the YM, Spectra/por, and Slide-A-Lyzer membranes was determined by incubating each molecule at a range of concentrations, 1–1000 nM, with each of the three membranes. The drug was allowed to incubate with the membrane in a volume of 500 μl for 30 minutes at 37° C. Following the incubation the samples were collected and the drug concentrations were calculated. The decrease in concentration was used to calculate the levels of binding to membrane.

Turning first to FIG. 1, there is shown a filter unit 5 suitable for use in the present invention. The filter unit shown is a MICROCON-10 filter unit commercially available from Millipore Corporation. It includes a sample reservoir 6, a base 8 situated below the sample reservoir 6 as depicted in the figure, and a membrane 7 separating the reservoir 6 from the base 8. The membrane is supported in the unit 5, and a liquid tight seal is provided between the periphery of the sample reservoir 6, the membrane 7 and the membrane support, such as with an O-ring. One or more filtrate ducts are provided in the unit 5 to allow the passage of filtrate from the membrane 7 into the base 8. Preferably the membrane is a retentive membrane, such as a YM membrane capable of retaining large molecules while allowing small molecules to pass through (the passage of small molecules through the membrane allows one to determine whether they have bound to the serum proteins, for example);

FIG. 2 illustrates the binding of molecules to such membranes. In particular, the binding of 50 biomolecules, a series of hydroxamic acids, was determined by incubating each molecule at a range of concentrations, 1–1000 nM, with each of the three membranes. The drug was allowed to incubate with the membrane in a volume of 500 $\mu$l for 30 minutes at 37° C. Following the incubation, the samples were collected and the drug concentrations were calculated. The decrease in concentration was used to calculate the levels of binding to membrane. In all cases, the YM membrane gives equivalent or lower binding of the small molecules than the Spectr/por or the Slide-A-Lyzer membranes. In most cases the YM membrane gives substantially lower binding.

In the preferred embodiment, the present invention provides a filter unit holder plate 20 (see FIGS. 4, 5 and 6) comprising a polymeric material, such as a polyolefin, PFA, PTFE, CORIAN or a thermoplastic, such as styrene, acetobutylstyrene, polycarbonate or acrylic, preferably a polyolefin, most preferably polypropylene. An additive which exhibits minimal or no binding characteristics with respect to biomolecules, for example proteins and/or DNA and/or RNA, is added to the polymeric material in an amount suitable to render the resulting blend non-binding. Suitable additives include Teflon® (tetrafluorethylene) resin, polyetheretherketone (PEEK), polyphenylene sulfide (PPS or RYTON), perfluoroalkyoxyalkane (PFA), fluorinated ethylenepropylene (FEP), and CORIAN (a mixture of natural minerals and pure acrylic). Preferably the polymer is polypropylene and (the additive is Teflon® resin.

The filter unit holder plate 20 contains a plurality of through-holes 21, such as 96 through-holes, wherein: each of said through-holes is capable of securely containing a filtration device, such as a Microcon-3, 10, 30 or 100® filter unit; said through-holes 21 containing an opening 22 on their bottom surface sufficient in size to allow the base 8 of said filter unit 5, but not the reservoir 6 or filter membrane 7 of said filter unit 5, to pass through the bottom surface and into a filtrate collection device (FIG. 5); said through-holes 21 preferably having a circular circumference; said through-holes 21 preferably being symmetrically arranged in the plate; and the center of each through-hole 21 being aligned vertically with the through-holes 21 in the rows above and below said through-hole and the center of each through-hole is aligned horizontally with the center of the through-holes in columns to the left and right of said through-hole 21.

Figure 5:
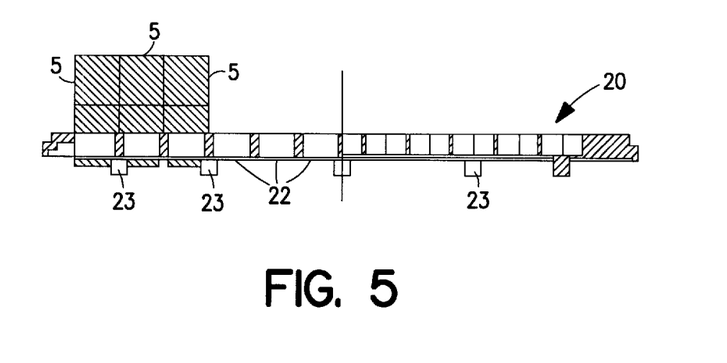
FIGS. 5, 5A—Filter Unit-holder. These diagrams are side (FIG. 5) and bottom (FIG. 5A) views of the holder. The side view illustrates the penetration of the Microcon filter units into the through-holes of the holder. The ridge of the filter unit lies on top of the through-hole and the base protrudes several millimeters. The bottom of the holder contains several protruding pegs which clamp into the filtrate collection plate. This allows the holder to fit tightly on top of the collection plate during centrifugation.
Figure 5A:
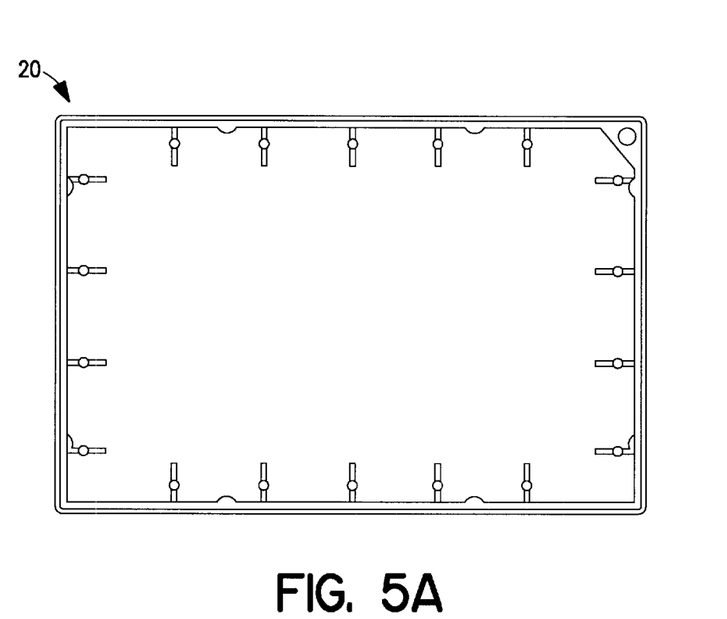
Figure 6:
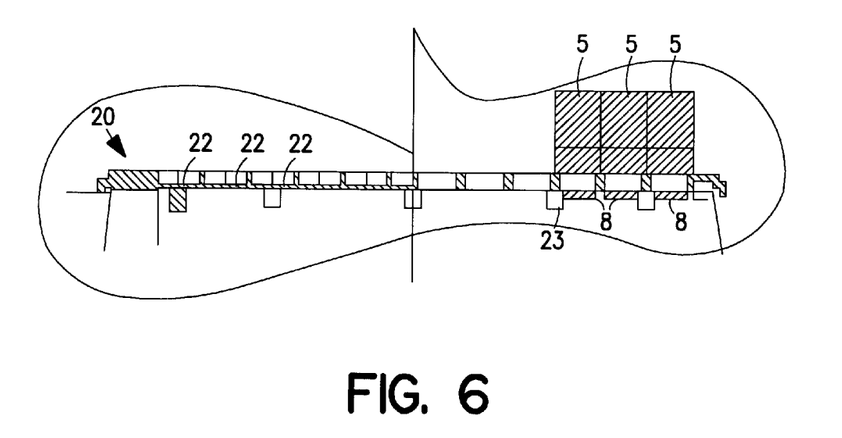
FIGS. 6, 6A—Filter Unit-holder. Illustrates assembly of the filter unit-holder and collection plate. The holder containing 96 Microcon units is placed on top of the collection plate. The base of the filter units protrudes into the through-holes and the pegs on the bottom of the holder seal the two parts.
Figure 6A:
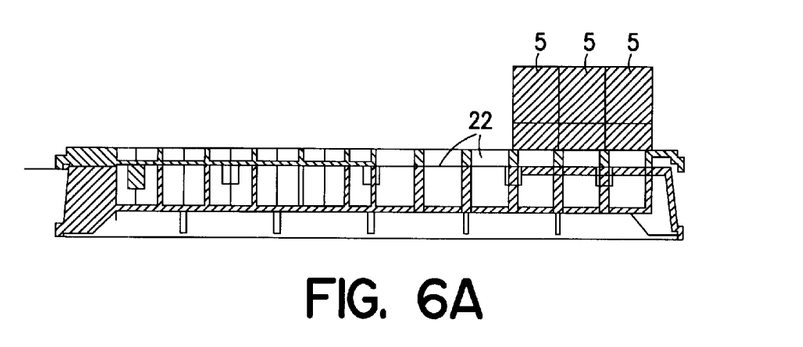
Figure 7:
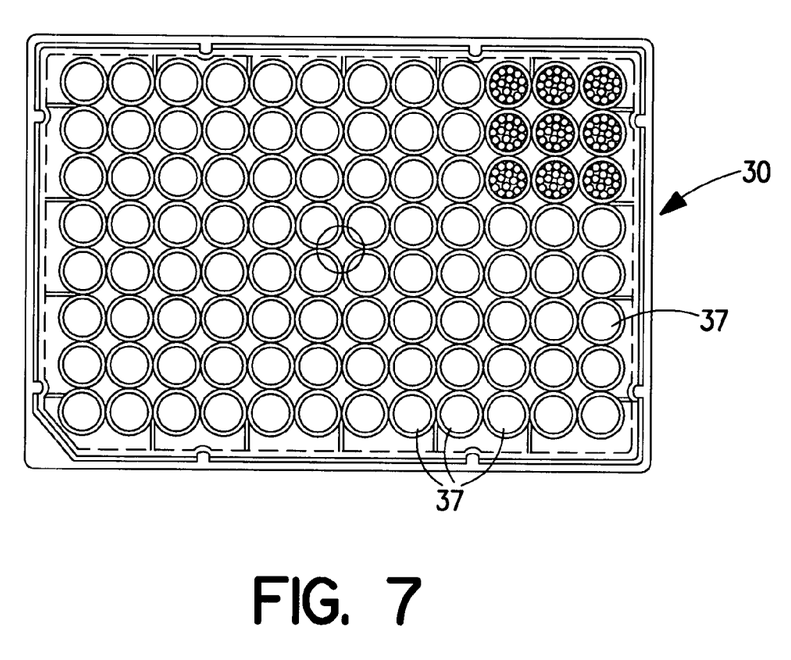
FIG. 7—Collection Plate. Top view of the collection plate containing a novel micro-array format which allows it to hold 96 Microcon filter units. The plate is compatible with the filter unit-holder. The plate contains bottom wells with the exterior dimensions of a standard 96-well plate. The wells can be flat, U-shaped, V-shaped or other shapes depending upon the application. The plate contains V-grooves which make the plate compatible with robotic arms.
Figure 8:
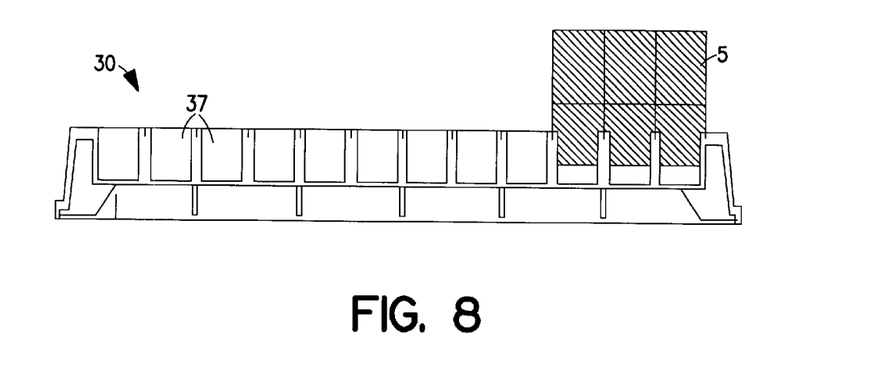
FIG. 8—The diagram is a side view of the collection plate. The plate is designed to hold 96 Microcon filter units. The filter unit can be directly inserted into the well. In the embodiment shown, the ridge of the filter unit lies on top of the outside of the well, allowing just the base of the filter unit to protrude into the wells. This feature prevents well-to-well spill-over during centrifugation of samples.
Figure 9:
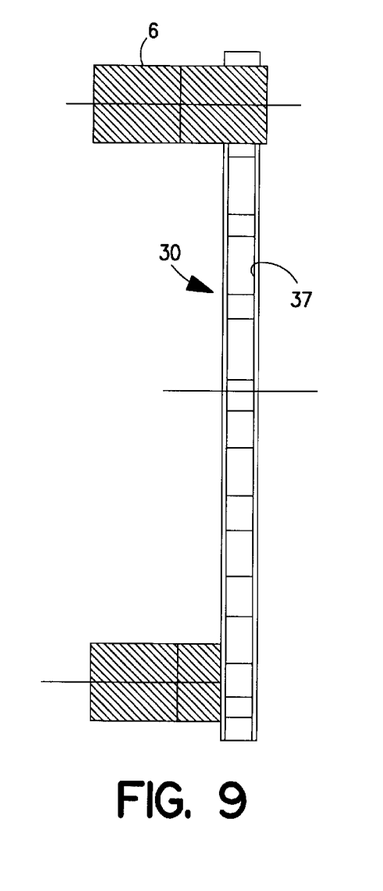
FIG. 9—Reversible-Well Collection Plate. The plate contains a novel micro-array format which allows it to hold 96 Microcon filter units. The holder contains 96 through holes where the bases of filter units pass through and protrude into the wells of the reversible-well collection plate for the retrieval of the filtrate. The holder also aligns the open end of the Microcon reservoirs which can also fit into the wells of the reversible well-collection plate. This feature makes the 96-well invert spin possible.
Figure 14A:
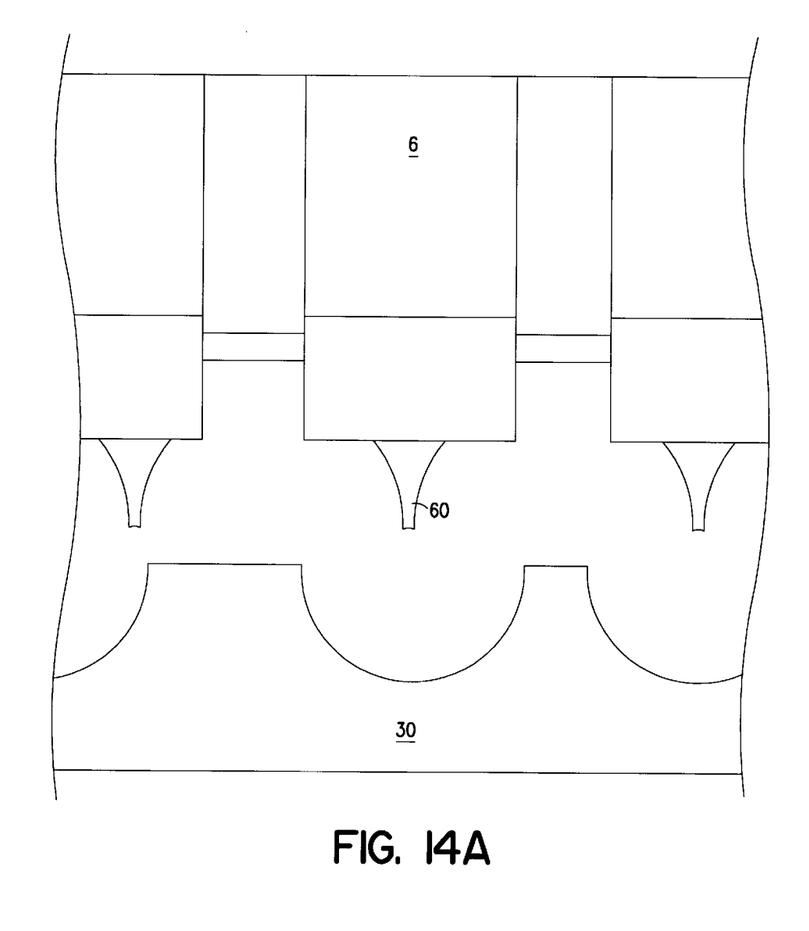
Figure 15:
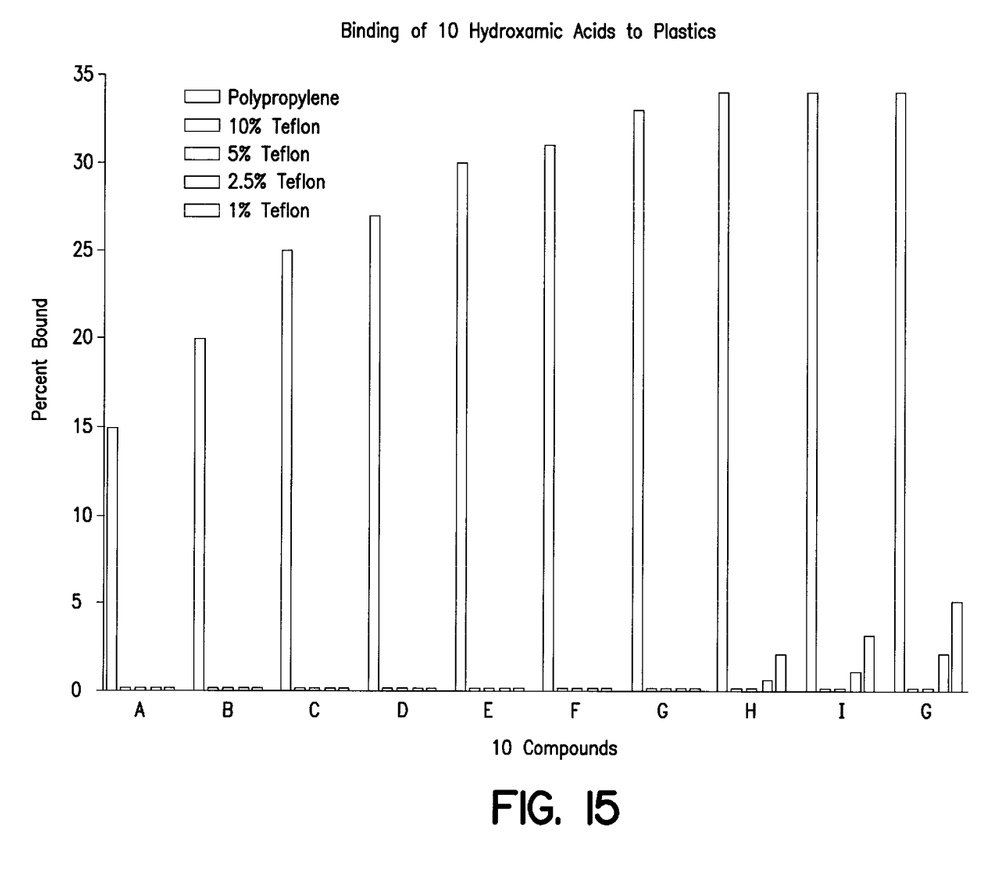
FIG. 15—Graph showing various amounts of TEFLON resin and the resulting binding for 10 different hydroxamic acids. The data show that virtually no binding resulted for all compounds tested when the amount of TEFLON resin was as low as 1%. Acceptable levels of binding for compounds H, I and J resulted even at TEFLON resin amounts as low as 2.5% and 1%.

As can be seen in FIGS. 5 and 6, each filter unit 5, and more particularly, the base 8 of each filter unit 5, sits in a respective opening 22 in each through-hole 21 of the filter unit holder 20. The outer diameter of the base 8 is slightly less than the diameter of the opening 22, allowing the base to tightly fit into the through-hole 21. Below the membrane 7, the base 8 has an outer diameter smaller than the outer diameter of the reservoir 6, thus forming a shoulder 9 (FIG. 1). The shoulder 9 lies on top of the opening 22, providing a vertical stop preventing the unit 5 from penetrating further into the well 21. Preferably the lower free end of the base 8 protrudes slightly through the opening 22 so that any filtrate flowing from the base flows into a corresponding well in the collection plate (discussed below) without leaking or contaminating other nearby wells. However, the filter unit 5 should not be inserted too deeply in the through-hole 21, since the O-ring used to seal the membrane in the unit 5 may be stressed and fail as a result. Alternatively, the lower free end of the base 8 could be substantially planar or planar with the bottom surface of the filter holder 20, and spouts 60 (FIGS. 14, 14A) could be used to direct the flow of filtrate in order to avoid cross-contamination. The spout 60 can be part of the filter unit 5, and positioned an optimum distance from the well of the collection plate into which the fluid will drop.

In one embodiment, the exterior bottom surface of said filter unit holder plate 20 contains a plurality of pegs 23 (FIG. 5) protruding therefrom sufficient in number and size to connect said plate to a reversible-well collection plate (said "reversible-well collection plate" is the reversible collection plate described and claimed herein). Alternatively, the collection plate surface can contain a plurality of nubs which are received in corresponding recesses in the bottom of the filter unit holder 20 to facilitate their assembly. The external dimensions of said filter unit holder plate 20 are about the same as the external dimensions of a standard 96-well plate used for high-throughput screening assays. Preferably, said filter unit holder plate 20 is composed of from about 1–10% Teflon® resin and from about 90–99% polypropylene, most preferably, of about 2.5% Teflon® resin and about 97.5% polypropylene. This combination of Teflon® resin inhibits the binding of molecules to the surface of the wells 21 of the plates, and thus makes for more efficient and reliable assays.

Figure 10:
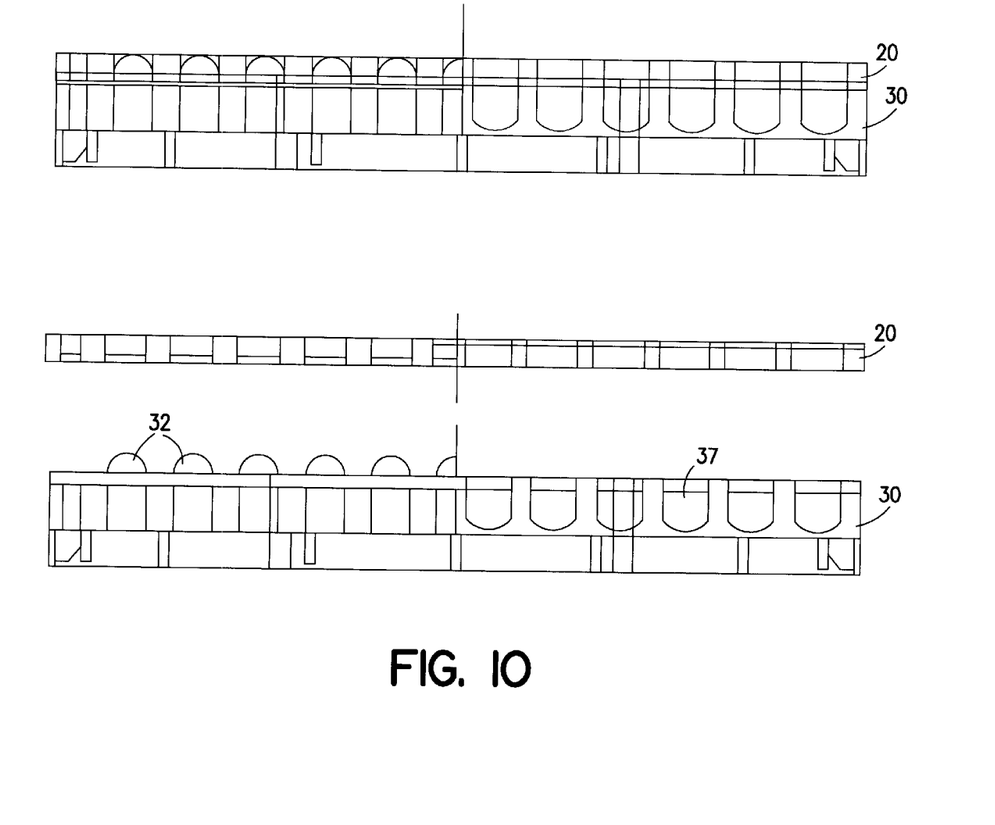
FIG. 10—Reversible-Well Holder. The diagram is a side view of the alignment of retentate holder and collection plate. The diagram illustrates that the micro-array format between the holder and collection plate is in alignment.
Figure 11:
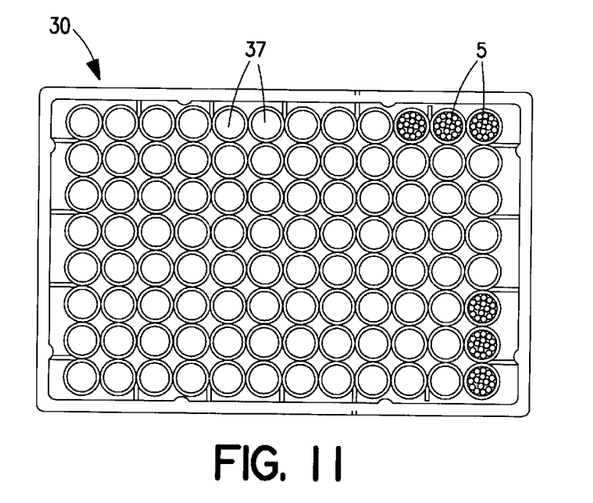
FIGS. 11, 11A and 11B—Top, front and side view of Reversible-Well Collection Plate. The collection plate contains a novel micro-array format which allows it to hold 96 Microcon filter units. The plate was designed to allow the wells to fit into either end of the filter units. Thus, in the preferred embodiment, the reversible-well collection plate can be used for the collection of both the filtrate and retentate. The plate is compatible with the reversible-well holder. The plate can contain U-bottom wells with the exterior dimensions of a standard 96-well plate. The plate also can contain V-grooves which make it compatible with robotic arms.
Figure 11A:
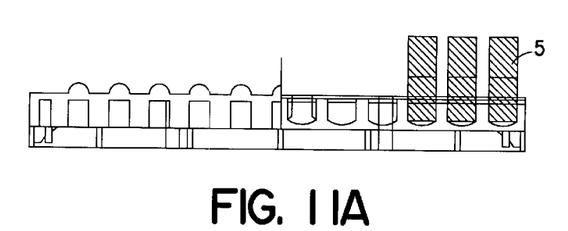
Figure 11B:
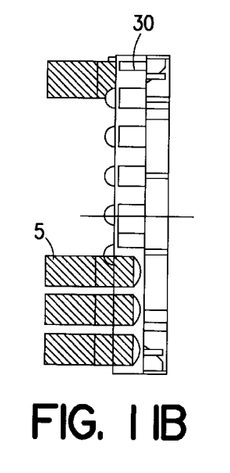
Figure 12:
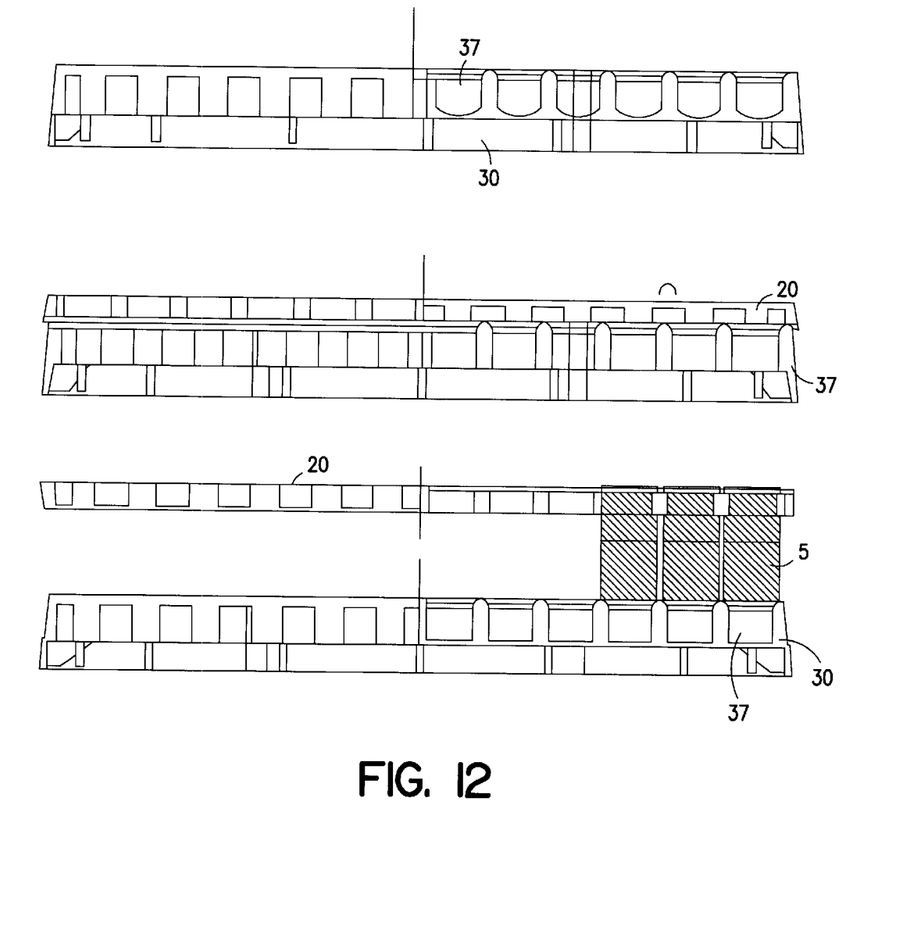
FIG. 12—Reversible-Well Collection Plate. The side view of the reversible-well collection plate illustrates how both sides of the Microcon filter units contained in the holder can fit into the wells. The raised bumps formed on the collection plate allow the open end of the Microcon reservoirs to fit tightly into the wells. This unique feature allows for the collection of both the filtrate and retentate in a single experiment without well to well spill over.

In the event contact of the sample with the filter holder plate 20 is unlikely, the use of the polymeric blend of the present invention is not necessary for this portion of the device. This invention also provides a collection plate 30 (FIGS. 6–12) which is preferably a reversible-well collection plate. Since the collection plate 30 will contact sample, it preferably comprises the polymeric blend of the present invention, most preferably polypropylene and Teflon® resin. The collection plate 30 also preferably contains a plurality of wells 37, wherein: each of said wells 37 is capable of securely containing a Microcon-3, 10, 30 or 100® filter unit; the top of each said well 37 is capable of securely containing either end of the filter unit; wherein the wells 37 can have a U-shaped bottom surface sufficient to allow said surface to securely contain either end of said filter unit; and wherein:

the side and bottom surfaces of said filtrate collection plate can contain a plurality of V-shaped grooves sufficient in number and size to allow the plate to be manipulated by a standard robotic or automated device; and, the external dimensions of said filtrate collection plate are about the same as the external dimensions of a standard 96-well plate. As shown in FIG. 10, the collection plate 30 preferably includes a plurality of aligned semi-circular in cross-section pins 32 which assist in aligning the collection plate 30 underneath the holder 20, or on top of the filter units 5 during recovery. Each of the pins 32 is centrally positioned about four symmetrical wells 37, and is dimensioned to fit between four corresponding filter units 5 in the recovery mode. Preferably, the plate is composed of from about 1–20% Teflon® resin and from about 80–99% polypropylene, more preferably 1–10% Teflon resin and 90–99% polypropylene, most preferably, about 2.5% Teflon® resin and about 97.5% polypropylene. Binding performance must be weighed against cost in determining optimum amounts of TEFLON resin. Other plastics and additives mentioned above with respect to the filter unit holder 20 are also suitable materials of construction for the collection plate. Preferably, the filter unit is a Micron-10® filter unit. A reversible-well collection plate comprising polypropylene and Teflon® resin and containing 96 wells substantially as shown in FIGS. 9, 10, 11 and 12 is particularly preferred.

Those skilled in the art will appreciate the filter unit also can be constructed of the polymeric blend of the present invention.

The filter unit holder and collection plates are designed to work, in connection with filter units, together in high-throughput screening assays for separating out small molecules ("small" generally meaning molecules having a molecular weight of about 300–600 daltons, although smaller and larger molecules may be separated as well) which bind to certain proteins from those which don't. Thus, this invention further provides a high-throughput screening assay for the detection of the binding of small molecules to protein which comprises the steps of:

(a) loading a sample of liquid containing the small molecule into a sample preparation device such as a Microcon-3, 10, 30 or 100® filter unit having a membrane which retains molecules of a certain molecular weight;

(b) placing said loaded filter unit of step (a) securely into the filter unit holder plate 20 of the present invention;

(c) securely attaching the bottom of said loaded filter unit holder plate of step (b) to the top of the reversible-well collection plate of the present invention, such that the base of said filter unit protrudes through the bottom of the filter unit holder plate (in the embodiment where some other means to direct filtrate is not used) and fits securely into the wells of the reversible-well collection plate;

(d) collecting the filtrate from the wells of the collection plate so as to determine the small molecules which do not bind ("free") to the protein, wherein said collection is by centrifuging the plate combination of step (c) for a period of time sufficient to allow the free small molecules to pass through the filter membrane and into the collection wells, while not allowing substantially any of the bound small molecules to pass through the membrane; and, (e) collecting the bound molecules from step (d), wherein said collecting is by connecting the wells of a second reversible-well collection plate, said wells facing down, securely to the top ends of the filter units, securely inverting the filter unit/reversible-well combination and then centrifuging the inverted combination for a period of time sufficient to allow the bound small molecules to pass into the wells of the collection plate.

Said assay is readily conducted by ordinarily skilled artisans given the teachings of this invention and without undue experimentation. For example, said artisans are well able to determine sufficient centrifuging speeds and time for both the filtrate collection (e.g., 3000 rpm for 30 minutes) and retentate collection (e.g., five minutes) steps. Said assay offers a number of advantages not presently available in the high-throughput screening art. For example, due to the incorporation of Teflon® resin into both plates, small molecules are inhibited from sticking to the surfaces of the plates, wells, thus leading to more accurate assessments of free and bound molecules. Also, due to the nature of the structure of the wells of the reversible-well plates, having the capacity to attach to either end of the filter units, filtrate can be collected from the initial filter units in a convenient step.

The following examples further illustrate the nature of this invention. However, those of ordinary skill in the art will readily understand that these examples are merely illustrative of the invention as fully defined in the claims which follow thereafter.

EXAMPLES

Study 1

Use of Microcon-10 Filter Units Instead of Dialysis Tubing

The Microcon-10 filter units were purchased from Millipore Corporation (Danvers, Mass. catalogue #42407). The Microcon-10 filter device contains a low binding, anisotropic, hydrophilic-regenerated cellulose membrane (YM membrane) with a size exclusion of 10,000 daltons (FIG. 1). The sample reservoir containing the membrane was inserted into a microfuge tube. The sample reservoir will hold up 500 ul of solution. The liquid was passed through the size-exclusion membrane via centrifugation in a tabletop, micro-centrifuge.

The aim of the first experiment was to demonstrate that the YM membrane shows very low levels of binding to small molecules; if a membrane is shown to bind to a large number of different small molecules, the use of that membrane for determining an accurate protein binding value for a molecule is not possible. Binding properties of the YM membrane with that of two commercially available dialysis membranes, Spectra/Por (Spectrum, Laguna Hills, Calif. catlogue #132670) and Slide-A-Lyzer (Pierce, Rockford, Ill. catalogue #66426) were compared; both dialysis membranes contained a molecular weight cut-off of 10,000 daltons. Fifty small molecules, representing a series of hydroxamic acids, were tested for their ability to bind to the three different membranes. This was done by adding each molecule, ranging in concentration from 1–1000 nM, in a volume of 500 ul to each of the three membranes. The drugs were allowed to incubate in the membranes for 30 minutes at 37° C. Following the incubation, the amount of binding of the molecules to each membrane was calculated. This was done by removing the samples from the membranes and calculating the concentration of drug remaining by mass spectrometry or bio-assay (FIG. 2). The binding of molecules to the YM membrane was very low. Forty seven of the 50 molecules tested showed no detectable levels of binding, and three of the molecules showed 2, 3 and 4% binding, respectively. In contrast, the two other dialysis membranes showed very high binding—25 molecules showed greater than 10% binding to the Slide-A-Lyzer, with molecules 44 to 50 exhibiting greater than 25% binding. Similarly, the Spectra/Por membrane also showed very high binding—with 20 molecules exhibiting greater than 10% binding and molecules 44 to 50 showing greater than 20% binding.

Because of the high degree of binding exhibited by the Slide-A-Lyzer and Spectra/Por, the use of these membranes in a protein binding assay is unwise. For, example, determining accurate protein binding values for compounds 44–50 would be impossible using the Slide-A-Lyzer and Spectra/Por membranes. It would be very difficult to distinguish between how much of the molecule is bound to protein versus the membrane. In contrast, due to the low levels of binding to the YM membrane, using the Microcon-10 filter unit in a protein-binding assay would yield more accurate data.

The aim of the next experiment was to determine whether or not we could use the Microcon-10 filter units in an assay to calculate accurate protein binding values of small molecules. Also, to determine if the protein binding values generated using the Microcon-10 filter units is comparable to those values generated using the standard equilibrium dialysis method. In order to address the questions, 50 small molecules, ranging in molecular weight from 200 to 400 daltons were analyzed in parallel for binding to human serum proteins using the Microcon-10 filter units or equilibrium dialysis with the Spectra/por membranes. For the assay employing the Microcon-10 filter units, each of the 50 molecules were diluted to a final concentration of 1 uM into 500 ul of whole human serum. The samples were allowed to incubate for 30 minutes at 37° C. in an incubator. Following the incubation the samples were transferred to the Microcon-10 sample reservoirs and the free drug was separated from serum bound drug by spinning the filter units at 12,000 g at 37° C. for 10 minutes.

Twenty percent of the total volume (100 ul) was allowed to pass through and the drug concentration in the filtrate which contains the free, unbound molecule was calculated. The decrease in drug concentration in the filtrate is a measure of protein binding and is calculated by simply dividing the starting concentration (1 uM) by the concentration of drug in the filtrate. For the assay using equilibrium dialysis, each of the 50 molecules was diluted to a final concentration of 1 uM into 500 of whole human serum. The samples were allowed to incubate for 30 minutes at 37° C. in an incubator. Following the incubation, the samples were transferred to dialysis tubing with a surface area of 3 $cm^2$ and sealed with dialysis clamps. The tubing was placed in 4 litres of water that was pre-equilibrated to 37° C. Each 4-litre beaker contained 10 dialysis bags, and the samples were allowed to dialyze for 24 hours. Following the incubation, the samples were collected and the concentration of drug remaining in the bag was calculated.

Figure 3:
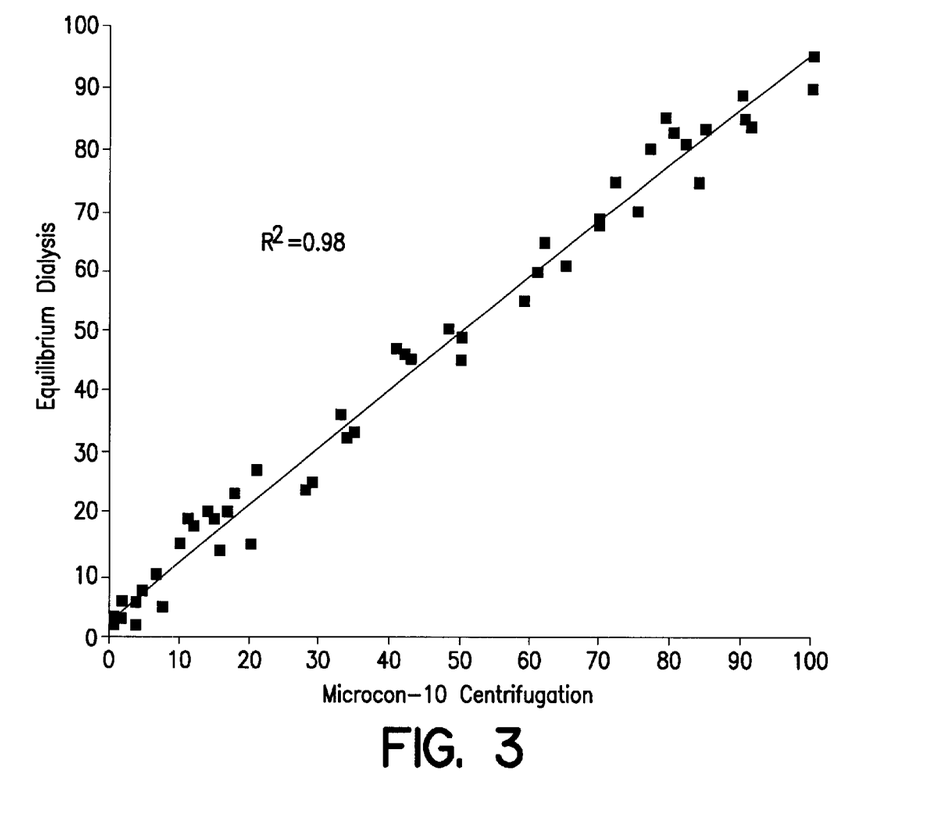
FIG. 3—Correlation Between Equilibrium Dialysis and Microcon-10 Centrifugation. The amount of serum binding of 50 small molecules was calculated using standard equilibrium dialysis and Microcon-10 centrifugation. The binding values generated in the two assays were compared and a correlation curve plotted. The $R^2$ value is 0.98.
Figure 4:
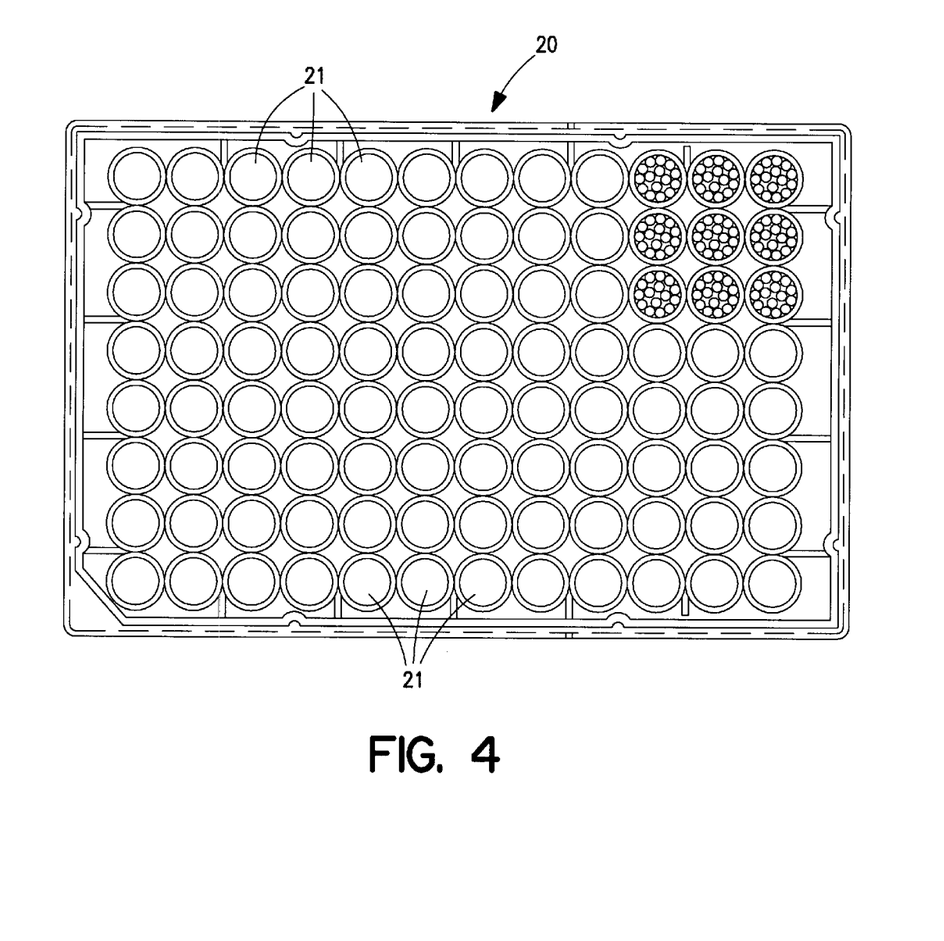
FIG. 4—Filter Unit-holder. Top view of the filter unit holder containing a novel micro-array format which allows it to hold 96 Microcon filter units. The holder contains 96 through holes where the base of the filter unit sits, and, in one embodiment, protrudes into the collection plate.

The decrease in drug concentration is measure of protein binding and is calculated by simply dividing the starting concentration [1 uM] by the concentration of drug remaining following dialysis. The protein binding values generated in both assays were compared (see FIG. 3). There is a strong positive correlation between the binding values generated using equilibrium dialysis and Microcon-10 centrifugation. The $R^2$ value is 0.98 for the 50 small molecules analyzed in the study. These data suggest that the Microcon-10 filter units can be used to calculate accurate protein binding values for small molecules comparable to equilibrium dialysis. However, there are also practical advantages in using the Microcon-10 devices for determining the protein binding of small molecules; these include speed of the assay and reduced set-up time.

Study 2

Formulation of Plasticware Capable of Reducing the Binding of Small Molecules to the Bottom of the Wells in the Collection Plates.

Both the retentate and filtrate collection plates were originally composed of pure polypropylene. However, following a protein-binding assay, the free drug contained in the filtrate showed binding to the surface of the well. This binding to polypropylene was seen for many small molecules. Therefore, in many cases the calculated concentration of drug in the filtrate was incorrect and lead to the extrapolation of erroneous protein binding values. In order to eliminate the binding of small molecules to the polypropylene plates a novel mixture of plastic was formulated. Teflon resin was mixed with pure polypropylene and used to make the retentate and filtrate plates. The hybrid plastic contained 2.5% Teflon resin and 97.5% polypropylene. In order to compare the binding properties of the hybrid plastic to that of pure polypropylene, the binding of 50 small molecules to both plastics were determined. This was done by incubating each of the small molecules at a range of concentrations (1–1000 nM) in the well of a plate composed of pure polypropylene or polypropylene with 2.5% Teflon. The small molecules were allowed to incubate in the well in a volume of 200 $\mu$l of water for 30 minutes at 37° C.

Figure 13:
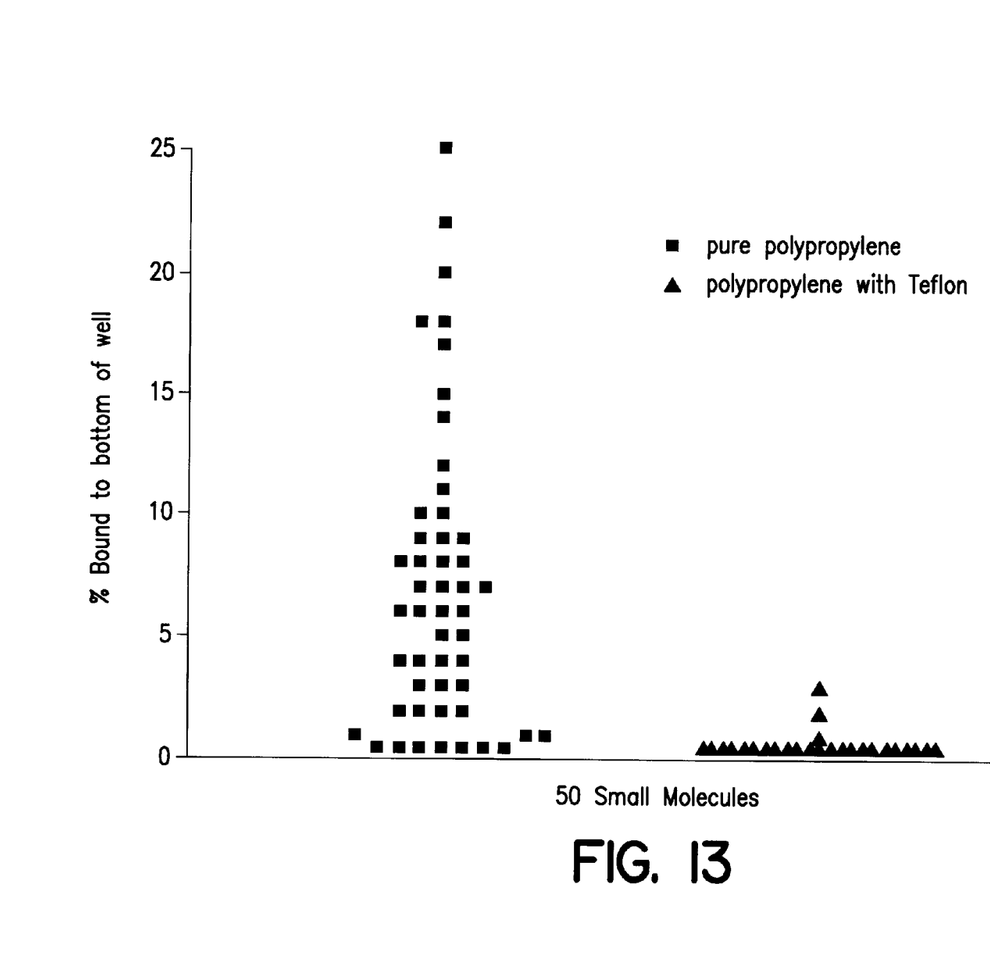
FIG. 13—Binding of Small Molecules to Polypropylene and Polypropylene with Teflon®. The binding of 50 small molecules to polypropylene and polypropylene with 2.5% Teflon was determined by incubating each molecule at a range of concentrations, 1–1000 nM, with each of two plastic plates. The drug was allowed to incubate in the well in a volume of 500 ul water for 30 minutes at 37° C. Following the incubation the samples were collected and the drug concentrations were calculated. The decrease in concentration was used to calculate the levels of binding to plastic.

Following the incubation the samples were removed from the wells and the concentration of drug was calculated using mass spectrometry or bio-assay. The incorporation of the Teflon resin eliminated binding to the surface of the wells almost completely (FIG. 13). These data suggest that the incorporation of Teflon resin into polypropylene plates will be very valuable in reducing binding of small molecules and other biomolecules to the bottom of the wells.

What is claimed is:

1. A sample preparation device comprising a liquid retaining device, said liquid retaining device comprising:

a substrate having at least a substrate well, said substrate being composed of a polymer having a first biomolecule binding capacity and an additive having a second biomolecule binding capacity less than said first biomolecule binding capacity, wherein said at least one substrate well is configured to receive a sample from said sample preparation device;

wherein said additive is selected from the group consisting of TEFLON(R)(tetrafluoroethylene) resin, polyetheretherketone, polyphenylene sulfide, perfluoroalkoxyalkane, fluorinated ethylenepropylene and CORIAN.

2. The device of claim 1, wherein said substrate is composed of from about 1–10% Teflon® resin and from about 90–99% polypropylene.

3. The device of claim 2, wherein said substrate is composed of about 2.5% Teflon® resin and about 97.5% polypropylene.

4. The device of claim 1, wherein said sample preparation device comprises a sample reservoir, a base, and a membrane between said sample reservoir and said base.

5. The device of claim 1, wherein said substrate has a plurality of substrate wells.

* * * * *